(12) United States Patent
Harraway

(10) Patent No.: US 7,918,993 B2
(45) Date of Patent: Apr. 5, 2011

(54) PORTABLE DIALYSIS MACHINE

(75) Inventor: James Harraway, Palmdale, CA (US)

(73) Assignee: James Harraway, Lancaster, CA (US)

( * ) Notice: Subject to any disclaimer, the term of this patent is extended or adjusted under 35 U.S.C. 154(b) by 0 days.

(21) Appl. No.: 10/053,920

(22) Filed: Jan. 24, 2002

(65) Prior Publication Data

US 2003/0136725 A1     Jul. 24, 2003

(51) Int. Cl.
*B01D 61/32*     (2006.01)
(52) U.S. Cl. ......... 210/85; 210/96.2; 210/143; 210/646; 345/173; 604/65; 704/270
(58) Field of Classification Search ............... 210/85, 210/87, 94, 96.1, 96.2, 101, 143, 321.71, 210/646, 647, 929; 604/4.01, 5.01, 6.01, 604/65, 67; 704/270, 274; 345/173
See application file for complete search history.

(56) References Cited

U.S. PATENT DOCUMENTS

| | | | |
|---|---|---|---|
| 3,809,241 A | 5/1974 | Alvine | 210/87 |
| 3,946,731 A | 3/1976 | Lichtenstein | |
| 4,083,777 A | 4/1978 | Hutchisson | 210/22 A |
| 4,144,165 A | 3/1979 | Matz | 210/22 C |
| 4,370,983 A * | 2/1983 | Lichtenstein | 210/929 |
| 5,024,756 A | 6/1991 | Sternby | 210/93 |
| 5,487,827 A | 1/1996 | Peterson et al. | 210/87 |
| 5,609,770 A | 3/1997 | Zimmerman et al. | 210/739 |
| 5,744,027 A | 4/1998 | Connell et al. | 210/96.2 |
| 5,788,851 A * | 8/1998 | Kenley et al. | 210/646 |
| 5,867,821 A * | 2/1999 | Ballantyne et al. | 705/2 |
| 5,895,571 A | 4/1999 | Utterberg | 210/241 |
| 6,577,899 B2 * | 6/2003 | Lebel et al. | 604/67 |
| 6,958,705 B2 * | 10/2005 | Lebel et al. | 340/870.07 |

* cited by examiner

*Primary Examiner* — Joseph W Drodge

(57) ABSTRACT

The portable dialysis machine may include an enclosure having a removable base. There may be a front panel having associated therewith multiple external connectors, smart function keys, a touch panel element and a voice activated sensor. The front panel may be in communication with an electronic circuit element having a controller in communication therewith. There may be a blood flow element and a hydraulic flow element. A water reservoir and power supply may be included. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

6 Claims, 3 Drawing Sheets

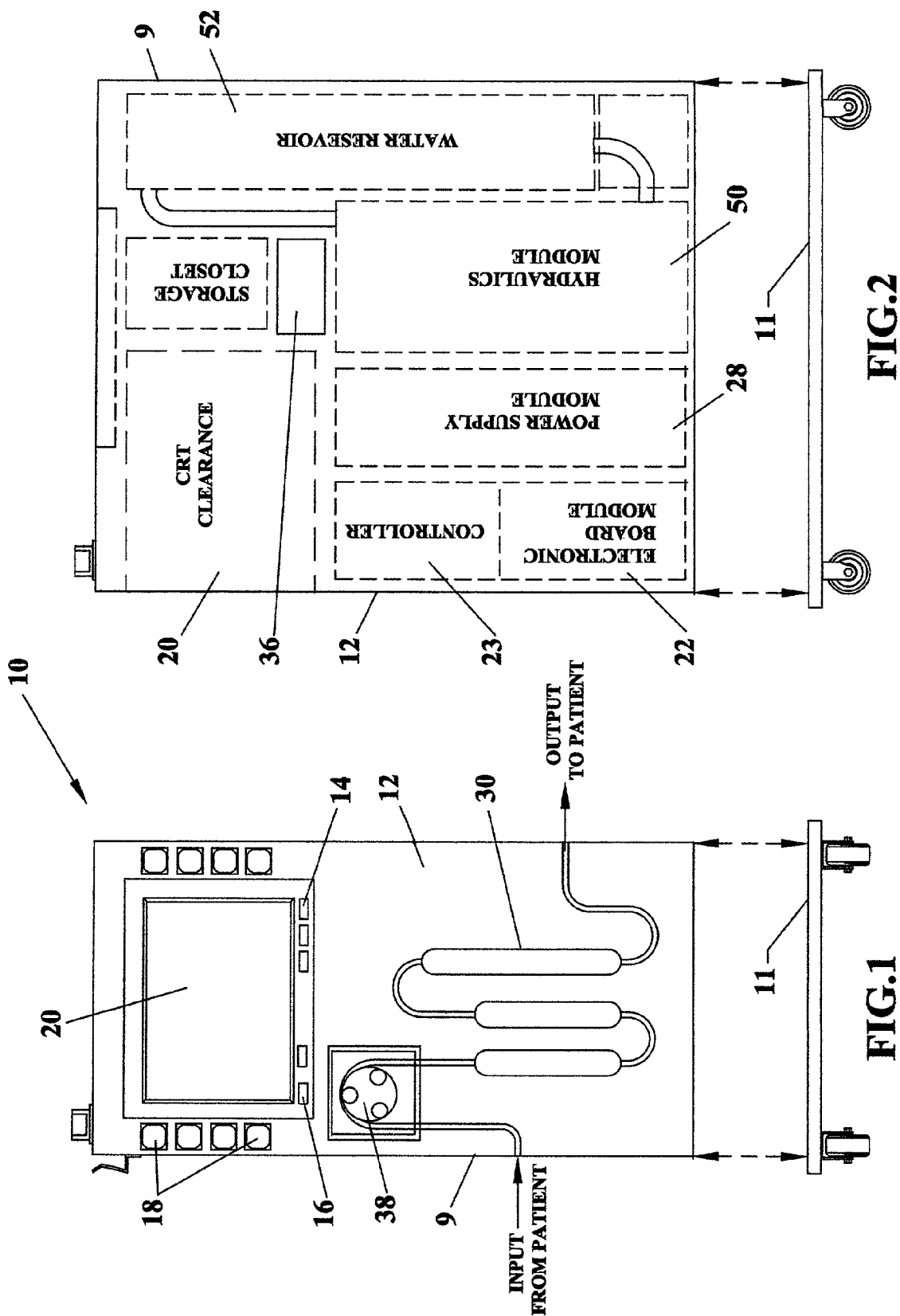

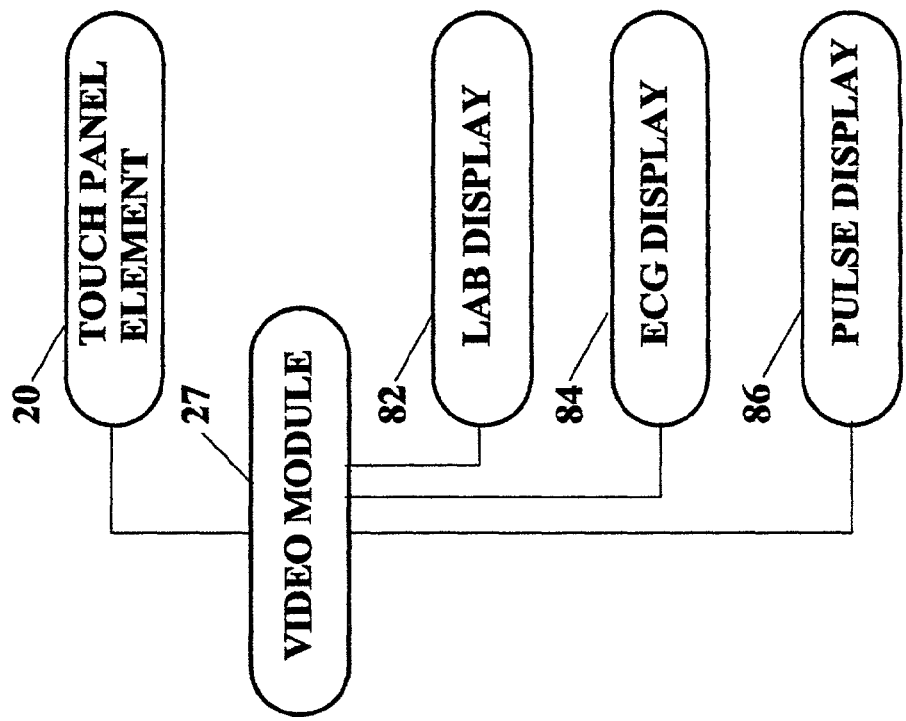
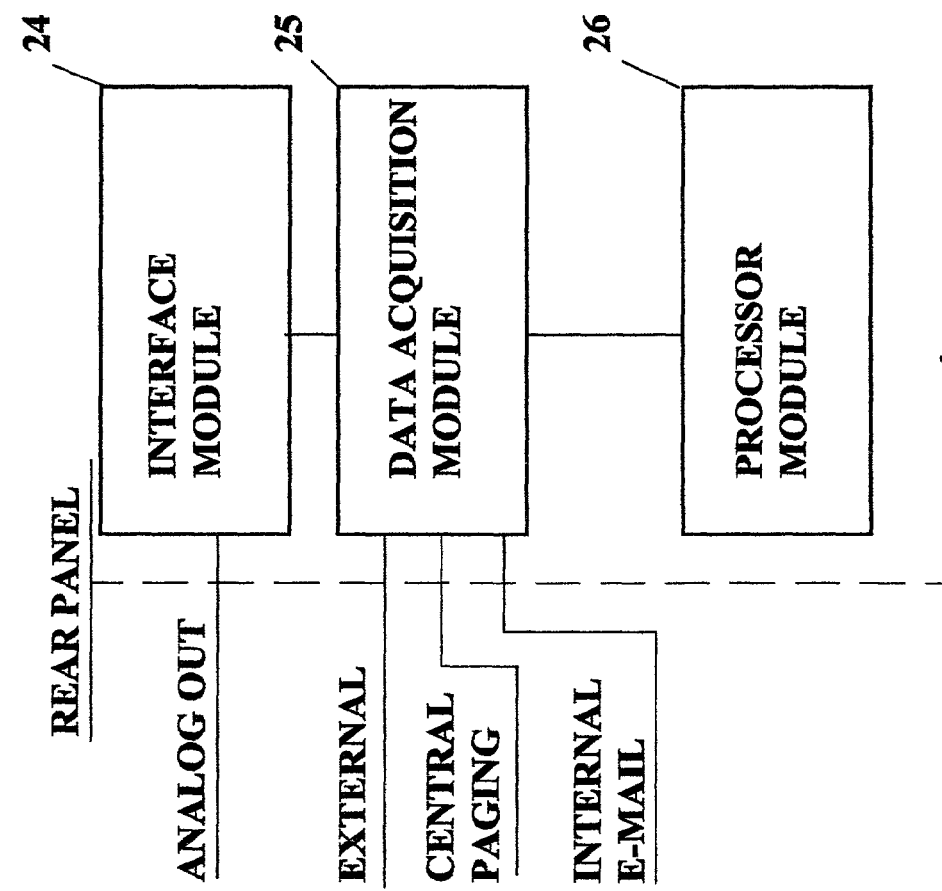

US 7,918,993 B2

PORTABLE DIALYSIS MACHINE

BACKGROUND OF THE INVENTION

This invention relates to kidney dialysis machines and more particularly to portable dialysis machines. The new dialysis machine includes additional sensor and monitor functions related to blood parameters and general client status during the dialysis process.

Various systems are used to accomplish the kidney dialysis operation and a variety of equipment configurations are currently known in the art. There are fairly simple portable dialysis machines as well as loosely integrated complex systems used in chronic care environments. Historically dialysis machines have operated with fixed operating parameter functions allowing little operator interaction. This was partially due to safety considerations, less need for operator training, and consistent, repeatable treatment of patients.

More recently it has been thought that more operator interaction for a particular patient may provide better treatment results. With the advent of the use of computers or smart controllers to aid the operator and to monitor safety concerns, it has become possible for more flexible, self-contained operator controlled dialysis machines. This is particularly true for portable dialysis machines that receive the benefit of the miniaturization of elements for use in such machines.

An example of a portable system which discloses a significant amount of operator control is disclosed in U.S. Pat. No. 5,609,770. This invention includes a dialysis machine mounted on wheels and having a touch panel display for operator interaction. The dialysis machine has one or more micro controllers to operate and control the hydraulic and blood flow paths. Also included is a safety or protective micro controller to monitor safety both in terms of operator actions and in equipment operation.

The system interface involves a touch screen display that includes display of images equivalent to labeled push button switches for the operator to select functions and set parameter values of the system. The dialysis machine includes many of the traditional monitor parameters and controls for dialysis machines that were preset and not available for direct operator control. However, the disclosure does not include or anticipate blood sampling and laboratory type analysis, pulse monitoring or electrocardiogram monitoring in dialysis machines. Also, use of voice activation technology by a patient in an emergency situation is not a functional element.

While systems for analysis of the hydraulic flow path have been disclosed as for example in U.S. Pat. Nos. 5,024,756 and 5,744,027, the evaluation of the blood parameters in the blood flow path to detect blood clotting, hemoglobin clotting time and triponet has not been implemented in currently known machines. Any such analysis is done separate from the dialysis unit. Performing blood tests such as blood clotting may improve the affectivity of the dialysis process in patient treatment.

The present invention may sample and test the blood of the patient during dialysis for evaluating dialysis affectivity and for input to adjust operational parameters. Monitoring of the patient pulse and ECG data to monitor patient well being during the dialysis process may be performed. There may be improved safety of use of dialysis machines in situations wherein the patient is not continuously monitored by a human operator.

As can be seen, there is a need for an integrated, portable dialysis machine that includes blood analysis, pulse monitoring and ECG monitoring.

SUMMARY OF THE INVENTION

The present invention dialysis machine may include an enclosure having a removable base. There may be a front panel having associated therewith multiple external connectors, smart function keys, a touch panel element and a voice activated sensor. The front panel may be in communication with an electronic circuit element having a controller in communication therewith. There may be a blood flow element and a hydraulic flow element. A water reservoir and power supply may be included.

These and other features, aspects and advantages of the present invention will become better understood with reference to the following drawings, description and claims.

BRIEF DESCRIPTION OF THE DRAWINGS

FIG. 1 illustrates a front elevation view according to an embodiment of the invention;

FIG. 2 illustrates a side elevation view thereof;

FIG. 4 is a schematic diagram of elements of an electronic board element according to an embodiment of the invention;

FIG. 5 is a schematic diagram of a video module interface according to an embodiment of the invention.

DESCRIPTION OF THE PREFERRED EMBODIMENT

Figure 3:
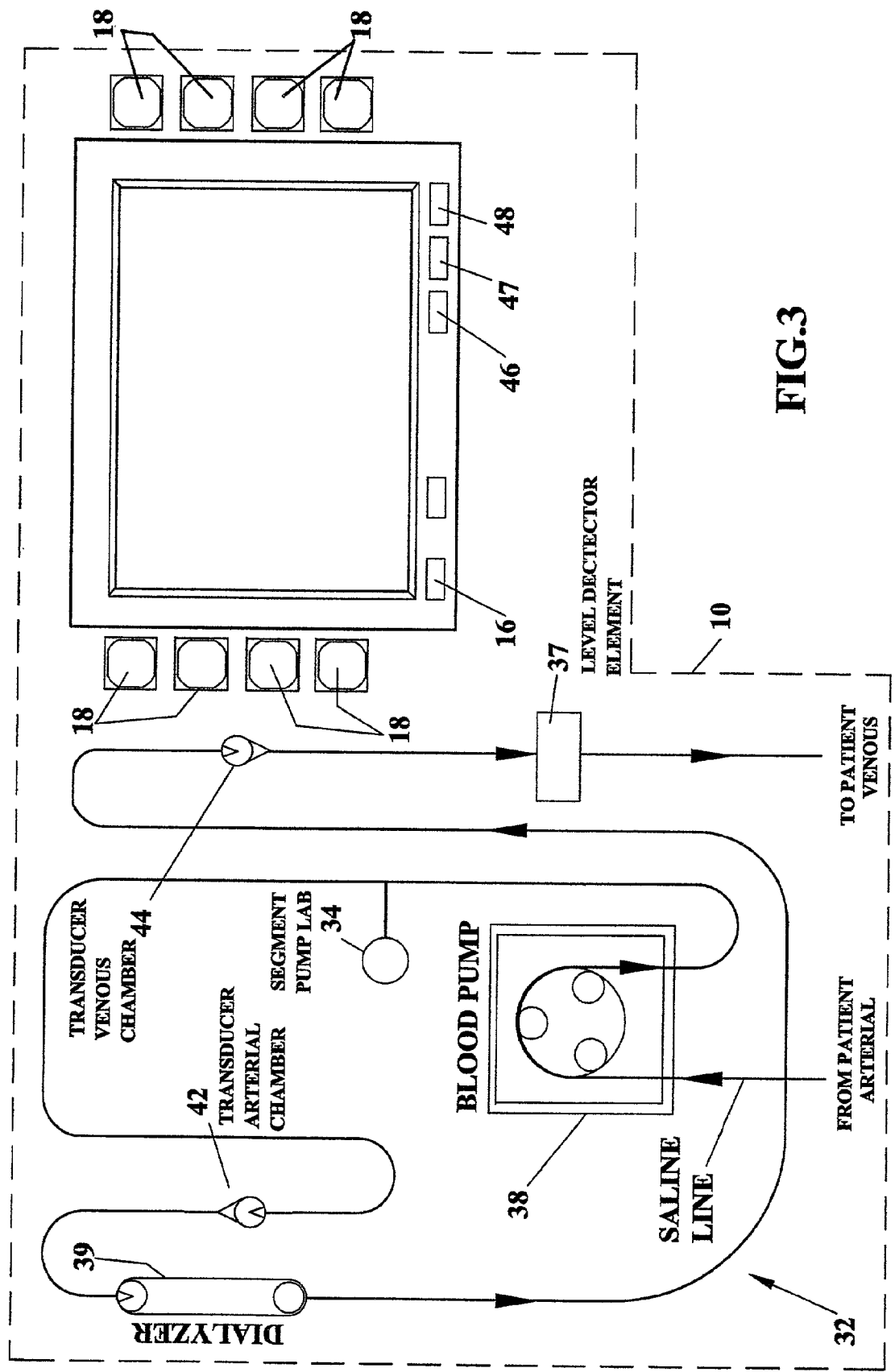
FIG. 3 illustrates a functional schematic diagram of the blood flow path of the dialysis machine according to an embodiment of the invention.

The following detailed description is the best currently contemplated modes for carrying out the invention. The description is not to be taken in a limiting sense, but is made merely for the purpose of illustrating the general principles of the invention.

Referring to FIG. 1, a dialysis machine 10 has a touch panel control element 20 for display and control in cooperation with a controller (not shown). The controller may be programmed with patient information and to display the traditional parameters used in dialysis that may then be set to required values for a particular patient to be treated. Also, parameters to be continuously monitored such as patient treatment as well as alarm parameters may be displayed and controlled. The portable dialysis machine 10 is mounted on a removable base 11.

There may be provision for smart function keys 18 for use in communication between Ethernet and the data acquisition board, central paging of a doctor and e-mail to the touch panel element 20. There may be also front panel connectors 14 for blood pressure, pulse and ECG input devices. Also a printer connector 16 may be included on the front panel 12 of the dialysis machine 10. There is front panel 12 access to the blood flow element 30 of the dialysis machine 10.

Referring to FIG. 2, the general arrangement of elements is illustrated. The touch panel element 20, electronic board module 22 that includes the controller 23 and the power supply 28 may generally be located in the front portion of the enclosure 9. Space is also allocated behind the front panel 12 for the blood flow element 30. The hydraulic flow element 50 is located behind the blood flow element 30. A water reservoir 52 may be located in the rear of the enclosure 9.

The electronic board element 22 may be further partitioned into an interface module 24, a data acquisition module 25, a processor module 26 and a video module 27 as illustrated in FIGS. 4 and 5. The processor module 26 may control the data acquisition module 25 communication with an external Ethernet, central paging system, e-mail system and the interface module 24. The interface module may in turn communicate with external analog equipment. The video module 27 may control the touch panel element 20 as well as an external laboratory display 82, ECG display 84 and pulse display 86. The power supply 28 may be connected to a dialysis pump, valves, balancing chamber, heparin pump, laboratory segment, heater, hydraulics, and conductor and temperature probes.

Referring to FIGS. 2 and 3, a port 34 may be included in the blood flow path 32 to sample blood for laboratory analysis. A blood analysis device 36 may be incorporated in the enclosure 9 and the results of a blood analysis communicated to the controller 23. The blood sample may also be sent separately to a laboratory for analysis. Particular blood analysis parameters to be checked during dialysis include blood clotting, hemoglobin clotting time and triponet for evaluation of blood count, blood clotting time and patient heart distress such as a heart attack.

The blood analysis allows operator interaction to correct for blood clotting and other measured parameters while the patient is being dialyzed. If specified alarms occur the patient may be immediately sent to the hospital for corrective measures. The set measured parameters may allow the user to make life saving decisions. An arterial chamber transducer 42 and venous chamber transducer 44 may be included in the blood flow path 32 for use in monitoring blood flow pressure changes. If blood clotting occurs, the arterial chamber transducer 42 may register a positive pressure change. An alarm and control circuit may stop the dialysis machine 10. If the patient's veins collapse, the venous chamber transducer 44 may register a negative pressure change. An alarm and control circuit may stop the dialysis machine 10. The blood flow path 32 includes a blood pump 38, dialyzer 39 and level detection check element 37. The blood flow path 32 is in fluid communication with the patient blood system.

Connectors 14 include a blood pressure device input 46, a pulse device input 48 and an ECG device input 47. The information produced by these monitoring devices may be processed by the controller 23 for operator display and to signal alarm conditions and/or to alter dialysis machine 10 operation in the event of a sensed patient problem. The integration of these additional monitoring devices provides additional information of blood clotting, blood clotting time and triponet for use by the operator in monitoring blood clotting conditions and possible heart attack.

A voice activated sensor 80 may be provided for use in an emergency as for example when the patient may be temporarily unattended. In the instance of a perceived problem on the part of the patient such as blood clotting or vein collapse the patient may voice instruct the dialysis machine 10 to revert to shut down as a fail safe mode.

While the invention has been particularly shown and described with respect to the illustrated and preferred embodiments thereof, it will be understood by those skilled in the art that the foregoing and other changes in form and details may be made therein without departing from the spirit and scope of the invention.

I claim:

1. A dialysis machine for performing kidney dialysis comprising:
    an enclosure having a removable base and comprising:
        a front panel having associated a plurality of connectors, a plurality of smart function keys, a touch panel element and a voice activated sensor,
        said front panel in communication with an electronic circuit element having a controller in communication therewith;
        a blood flow element;
        a hydraulic flow element; and
        a water reservoir and a power supply.

2. The dialysis machine as in claim 1 wherein said electronic board element further comprising:
    a processor module in communication with a data acquisition module; and
    said data acquisition module in communication with an interface module.

3. The dialysis machine as in claim 1 wherein said electronic board element further comprising a video module in communication with said touch panel element, a laboratory display, an ECG display and a pulse display.

4. The dialysis machine as in claim 1 wherein said plurality of connectors comprise a blood pressure device input, an ECG device input and a pulse device input.

5. The dialysis machine as in claim 1 wherein said blood flow element comprising:
    a blood pump and a dialyzer;
    an arterial chamber having a transducer and a venous chamber having a venous transducer;
    a port; and
    said blood flow element in communication with said electronic board element and connectable to a patient blood flow system.

6. A dialysis machine for performing kidney dialysis comprising:
    an enclosure having:
    a blood flow element in communication with an electronic circuit element and a front panel having a touch panel display and control element; and
    said blood flow element comprising:
    a serial blood flow path;
    a blood pump and a dialyzer;
    an arterial chamber having a transducer and a venous chamber having a venous transducer; and
    a port and said blood flow element connectable to a patient blood flow system.

* * * * *